United States Patent [19]

McQueen et al.

[11] Patent Number: 5,108,398

[45] Date of Patent: Apr. 28, 1992

[54] ORTHOPAEDIC KNEE FUSION APPARATUS

[75] Inventors: David A. McQueen; Francis W. Cooke, both of Wichita; Dustan L. Hahn, Derby, all of Kans.

[73] Assignee: Orthopaedic Research Institute, Wichita, Kans.

[21] Appl. No.: 598,920

[22] Filed: Oct. 16, 1990

[51] Int. Cl.$^5$ .................................. A61B 17/58
[52] U.S. Cl. ........................... 606/62; 606/64; 606/98; 606/105
[58] Field of Search ............... 606/60, 62–68, 606/90, 96–98, 104, 105; 623/18, 20

[56] References Cited

U.S. PATENT DOCUMENTS

| | | | |
|---|---|---|---|
| 2,821,979 | 2/1958 | Cameron | 606/64 |
| 4,016,874 | 4/1977 | Maffei et al. | 606/62 |
| 4,467,794 | 8/1984 | Maffei et al. | 606/62 |
| 4,541,424 | 9/1985 | Grosse et al. | 606/98 |
| 4,574,795 | 3/1986 | Georges | 606/64 |
| 4,622,959 | 11/1986 | Marcus | 606/98 X |
| 4,852,558 | 8/1989 | Outerbridge | 606/75 |
| 4,938,768 | 7/1990 | Wu | 606/60 X |

FOREIGN PATENT DOCUMENTS

| | | | |
|---|---|---|---|
| 311555 | 4/1989 | European Pat. Off. | 606/60 |
| 385580 | 6/1973 | U.S.S.R. | 606/62 |
| 1007659 | 3/1983 | U.S.S.R. | 606/62 |

OTHER PUBLICATIONS

Arthrodesis of the Knee, John Charnley, F.R.C.S., Clin. Orthop., 18: pp. 37–42, 1960.
Arthrodesis of the Knee with Intramedullary Nail Fixation, Robert Maxet, Jr., MD, and Marshall R. Urist, M.D. Dlin. Orthop., 18: pp. 43–54.
Arthrodesis of the Knee, David P. Green, M.D. James C. Parkes, II, M.D. and Frank E. Stinchfield, M.D., The Journal of Bone and Joint Surgery, vol. 49–A, No. 6, Sep. 1967, pp. 1065–1078.
A Study of the End–Results of Compression Arthrodesis of the Knee, John Charnley and H. G. Lowe, The Journal of Bone and Joint Surgery, vol. 40B, No. 4, Nov. 1958, pp. 633–635.
Arthrodesis of the Knee following Failed Total Knee Arthroplasty, Mark P. Brodersen, M.D., Robert H. Fitzgerald, Jr., M.D., Lowell F. A. Peterson, M.D., Mark B. Coventry, M.D., and Richard S. Bryan, M.D., The Journal of Bone and Joint Surgery, vol. 61–A, No. 2, Mar. 1979, pp. 181–185.

Primary Examiner—Robert A. Hafer
Assistant Examiner—Kevin G. Rooney
Attorney, Agent, or Firm—Hovey, Williams, Timmons & Collins

[57] ABSTRACT

An orthopaedic surgical implant apparatus includes an elongated intramedullary rod assembly 10 for use in uniting a pair of bone segments wherein each of the bone segments includes a medullary cavity. The elongated intramedullary rod assembly 10 defines a central longitudinal axis when assembled and includes first and second points of attachment 26, 48, the rod assembly 10 being adapted to be positioned within the medullary cavities of the bone segments and secured to the first bond segment at the first point of attachment 26 and to the second bone segment at the second point of attachment 48. Structure 18, 52 is provided for shortening the predetermined distance between the first and second points of attachment 26, 48 of the rod assembly in the direction of the longitudinal axis after the rod assembly has been connected to the first and second bone segments so that the first and second bone segments are brought into contact with and press against one another. A method of implanting the apparatus is also disclosed.

11 Claims, 4 Drawing Sheets

ORTHOPAEDIC KNEE FUSION APPARATUS

BACKGROUND OF THE INVENTION

1. Field of the Invention

The present invention relates generally to orthopaedic surgical implant devices and, more particularly, to an implant apparatus for use in uniting a pair of bones or bone segments wherein each of the bones or segments includes a medullary cavity.

2. Discussion of the Prior Art

Arthrodesis of the knee, or knee fusion, is a surgical procedure usually performed as a method of salvaging a severely damaged knee which is unstable or which is painful and limited in motion, and has possibly had many previous surgeries. Knee fusion is obtained by techniques which immobilize the joint as rigidly as can be obtained after excising bone, if necessary, from the femur and tibia at their interface. Bone fracture healing is achieved in a similar manner by positioning two fractured bone segments in close contact with one another and immobilizing the bone until fusion of the segments is achieved.

Conventional techniques for knee fusion include the use of devices for external and internal fixation of the joint. An external fixation device which provides compression to the joint was introduced by J. A. Key and John Charnley. According to these methods, pins are inserted through the long bones above and below the joint to be fused. Thereafter, an external fixator or frame is applied to the pins and compression of the joint is obtained by securing the fixator or frame relative to the pins and pulling the pins toward one another.

Although devices used in carrying out this known technique have been successful in achieving fusion of a knee joint, several drawbacks exist which suggest the need for an improved technique and apparatus. For example, it is necessary in the known devices to employ a framework which is retained in a position external to the skin of the knee joint for a period of several weeks or months beyond surgery. Thus, it is difficult to protect against infections and the patient is constantly in a position of discomfort.

A further drawback to the use of conventional external techniques resides in the inability of such techniques to provide reliable restraint of the joined bones or segments in all dimensions so as to prevent any substantial movement therebetween. For example, according to the abovedescribed technique a framework is attached between a pair of pins in such a way as to restrict relative axial movement of the femur and tibia, but fails to provide any substantial torsional or lateral support to the joint.

Internal fixation for knee fusion is conventionally achieved by passing an intramedullary rod, known to fracture fixation, into the femur and then in retrograde fashion, into the tibia. The ends of the rod are then secured with bone screws. This method imparts immediate stability to the joint, even in the case of failed arthroplasty where little cancellous bone may remain when the prosthesis has been removed.

The bone screws used to secure an intramedullary rod in place are inserted in a transverse direction to the rod and extend through the bone cortex on either side thereof. Known techniques for installing these bone screws require the use of X-rays to locate holes in the intramedullary rod through which the screws are to be passed so that holes may be drilled in the bone in alignment with the holes in the rod. Thus, these techniques require that the patient and surgical team be exposed to X-rays, and may involve the use of trial and error in aligning the drill with the holes in the rod.

Another problem encountered with known knee fusion devices arises as a result of the resorption of old bone which occurs as a result of the bones natural ability to rearrange its structure in a pattern which provides maximum strength while using a minimum of material. When an implant device is affixed to a bone it alters the manner in which that bone carries a load. This alteration in the load-bearing capacity of the bone, while potentially offering short-term benefits to the patient, may result in a combination of resorption of old bone and generation of new bone such that the bone is no longer able to support the implant device or the patient's activity, and failure occurs.

In an attempt to minimize the affect of an implant device on bone resorption where intramedullary rod devices are employed, it is known to either unfasten the bone screws from one end of the rod or to completely remove the rod after fusion has occurred so that compression of the bone is permitted when the bone is loaded. However, both of these known techniques require the use of additional surgery and its attendant risks.

In order to achieve fusion of a knee joint or proper fixation of a fractured bone, no separation between the bones or segments being joined may be permitted and only minimal displacement of the bones or segments should occur. When such a relationship between the bones or segments is not achieved, fibrous tissue can form at the desired fusion sight causing pain to the patient and impeding fusion.

OBJECTS AND SUMMARY OF THE INVENTION

It is an object of the present invention to provide an orthopaedic implant apparatus suitable for bone fracture healing and stabilization or fusion of joints and the surgical instrumentation required to implant the apparatus. The inventive construction incorporates advantageous features of known external fixation techniques by allowing active compression of joined bones or bone segments, while affording substantial lateral and torsional stability to the joined bones or segments.

It is another object of the present invention to provide an implant apparatus and accompanying surgical instrumentation which allows the device to be implanted without requiring the use of X-ray techniques which are time consuming and present dangers to those exposed to the X-rays.

Yet another object of the present invention is to provide an implant apparatus which inhibits longitudinal extension and lateral and torsional displacements of a pair of joined bones or segments while permitting relative compression of the segments in order to minimize the undesirable effects of bone absorption. Further, this object is achieved by the inventive construction through the use of an intramedullary rod assembly which obviates the need for an external fixator or frame to support the rod assembly.

In accordance with one aspect of the invention, an orthopaedic surgical implant apparatus is provided for use in uniting a pair of bone segments wherein each of the bone segments includes a medullary cavity. The apparatus comprises an elongated intramedullary rod assembly defining a central longitudinal axis when assembled and including first and second points of attachment. The rod assembly is adapted to be positioned within the medullary cavities of the bone segments and secured to the first bone segment at the first point of attachment and to the second bone segment at the second point of attachment. Tension means are provided for shortening the predetermined distance between the first and second points of attachment of the rod assembly after the rod assembly has been connected to the first and second bone segments so that the first and second bone segments are brought into contact with and press against one another.

Further, the apparatus may include shortening means for further reducing the predetermined distance between the first and second points of attachment after implantation of the apparatus when an axial compressive load is applied on the rod assembly. By providing this construction, when a compressive load is exerted on the first and second bone segments, the load is transmitted between the bone segments rather than through the rod assembly.

BRIEF DESCRIPTION OF THE DRAWING FIGURES

A preferred embodiment of the present invention is described in detail below with reference to the attached drawing figures, wherein.

DETAILED DESCRIPTION OF THE PREFERRED EMBODIMENT

Figure 1:
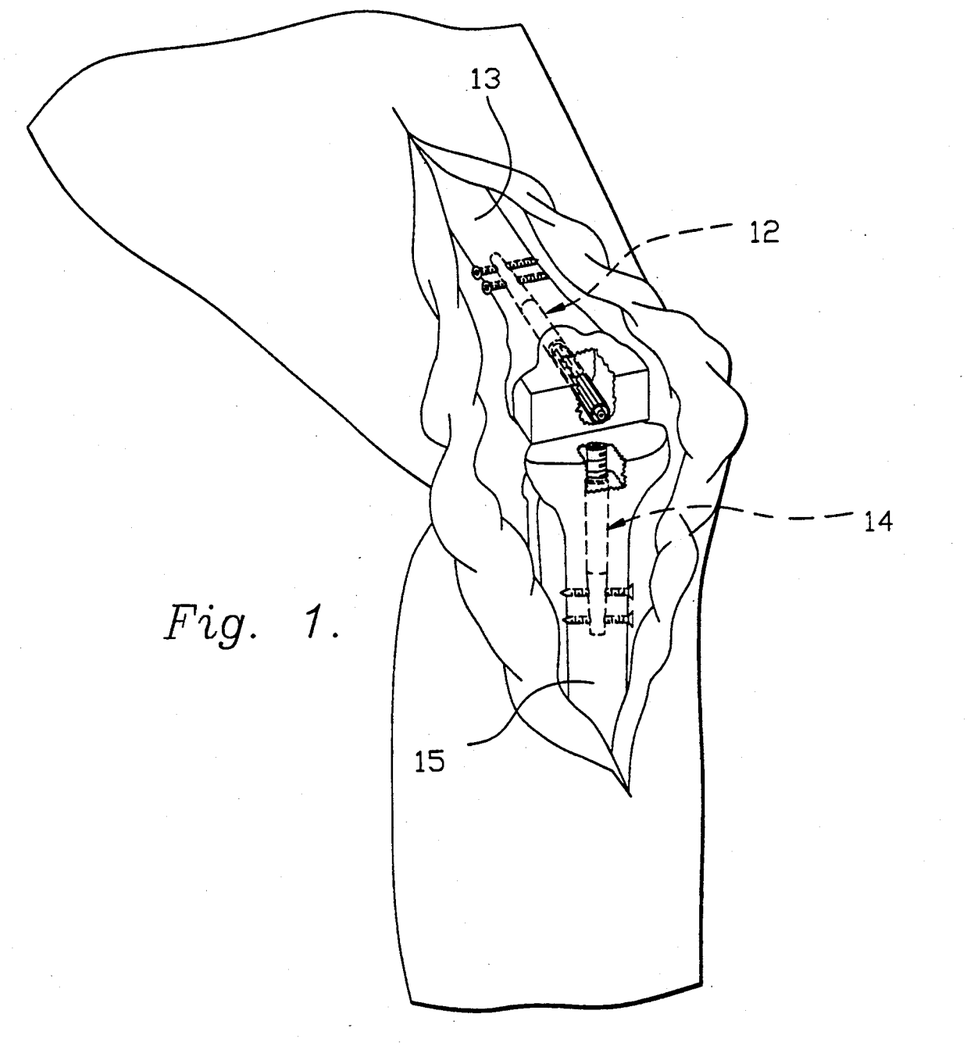
FIG. 1 is a perspective view of a dissected human knee joint provided with a partially assembled intrameddulary rod assembly constructed in accordance with the present invention.

An orthopaedic surgical implant apparatus constructed in accordance with a preferred embodiment of the invention is illustrated in FIG. 1. As shown in this figure, the apparatus is partially implanted in a femur 13 and tibia 15 of a human knee joint to be fused. However, it is understood that the apparatus of the present invention may also find application as an implant apparatus for use in the fixation of any fractured bone having a medullary cavity.

Figures 2, 3, 4, 5, 6:
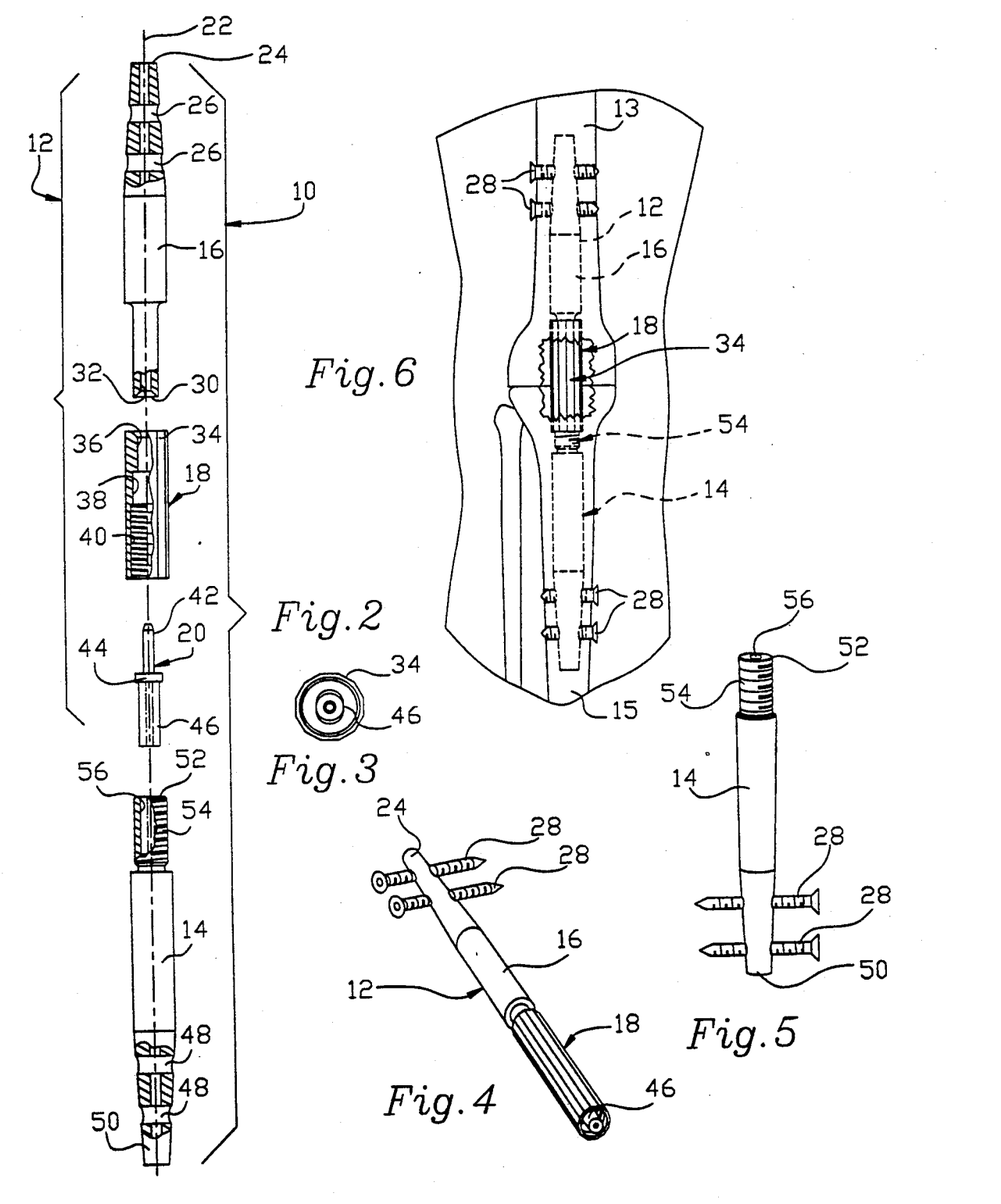
FIG. 2 is an exploded view, partially in section of the intramedullary rod assembly.
FIG. 3 is an end view of a femoral base assembly.
FIG. 4 is a perspective view of the femoral base assembly.
FIG. 5 is a perspective view of a tibial base of the intramedullary rod assembly.
FIG. 6 is a front elevational view of a human knee joint provided with a completely assembled intramedullary rod assembly constructed in accordance with the present invention.

The preferred apparatus includes an intramedullary rod assembly 10 as shown in FIG. 2, which includes a femoral base assembly 12 and a tibial base 14. The femoral base assembly 12 is comprised of a femoral base 16, a slider 18, and a femoral plug 20.

The femoral base 16 is of generally cylindrical shape defining a central longitudinal axis 22 and having a tapered proximal end 24 provided with a pair of holes 26 extending in a direction transverse to the axis for receiving screws 28 in a manner described more fully below and as illustrated in FIG. 4. Returning to FIG. 2, the femoral base 16 also includes a distal end 30 having an outer diameter which is reduced relative to the remainder of the femoral base for receiving the slider 18. Further, an axial bore 32 extends inward from the distal end 30 of the femoral base 16 and is provided with an inner diameter adapted to receive the femoral plug 20. Preferably, the femoral base 16 is hollow in order to reduce the weight of the device and to permit drainage of body fluids which might otherwise become trapped within the axial bore 32.

The slider 18 is of generally cylindrical shape having a multi-sided outer surface 34, as shown in FIG. 3, to permit gripping of the slider by a wrench or similar tool (not shown) of conventional construction, and includes a smooth proximal inner surface 36, shown in FIG. 2, having a diameter slightly larger than the outer diameter of the distal end 30 of the femoral base 16. By providing the slider 18 with this surface 36, the slider may be slidably received on the femoral base 16 and is freely rotatable relative thereto.

The femoral slider 18 also includes a smooth intermediate inner surface 38 of generally cylindrical shape which is provided with a diameter larger than the diameter of the proximal inner surface 36. Further, the slider includes an inner surface 40 at the distal end thereof which is threaded to receive a proximal end of the tibial base 14.

The femoral plug 20 is constructed with a solid cylindrical proximal end 42 having an outer diameter adapted to be received within the axial bore 32 of the femoral base to form a friction fit between the plug and the base. An intermediate annular shelf 44 is formed in the plug 20 adjacent the proximal end thereof and includes an outer diameter larger than the diameter of the proximal inner surface 36 of the slider 18 but slightly smaller than the diameter of the intermediate inner surface 38. By assembling the femoral plug 20 on the base 12 in this manner, the annular shelf 44 of the plug prevents the slider 18 from being removed from the base once the slider has been positioned on the base and the plug attached thereto. The femoral plug 20 also includes a hollow distal end portion 46 having a generally oval cross-sectional shape adjacent the annular shelf 44 and tapering off to a circular cross-sectional shape adjacent the distal end thereof, as shown in FIG. 3. The distal end of the femoral plug 20 is adapted to be received in a recess of the tibial base 14 as described below.

The tibial base 14 is a hollow generally cylindrical member having a pair of transverse holes 48 extending therethrough adjacent a tapered distal end 50 of the base. The transverse holes 48 are adapted to receive a pair of bone screws 28 as shown in FIG. 5. Further, a proximal end 52 of the base 16 includes a threaded outer surface 54 adapted to mate with the threaded inner surface 40 of the femoral slider 18 during implantation of the intramedullary rod assembly 10. Returning to FIG. 2, an oval-shaped bore 56 extends axially into the tibial base from the proximal end 52 and is sized to receive the distal end portion 46 of the femoral plug 20 and to prevent relative rotational movement between the femoral base 12 and the tibial base 14 when the oval-shaped portion of the plug is received in the oval bore.

Each of the components of the intramedullary rod assembly 10 are manufactured from material which is biocompatible with human tissue and which can provide sufficient mechanical strength to support the fused bone segments the material may either be metallic or non-metallic, and preferably are cast, forged, or rolled in cobalt-chromium, titanium, or other high strength stainless steel. High tolerance surfaces are then machined, ground and polished into the castings.

Figure 7:
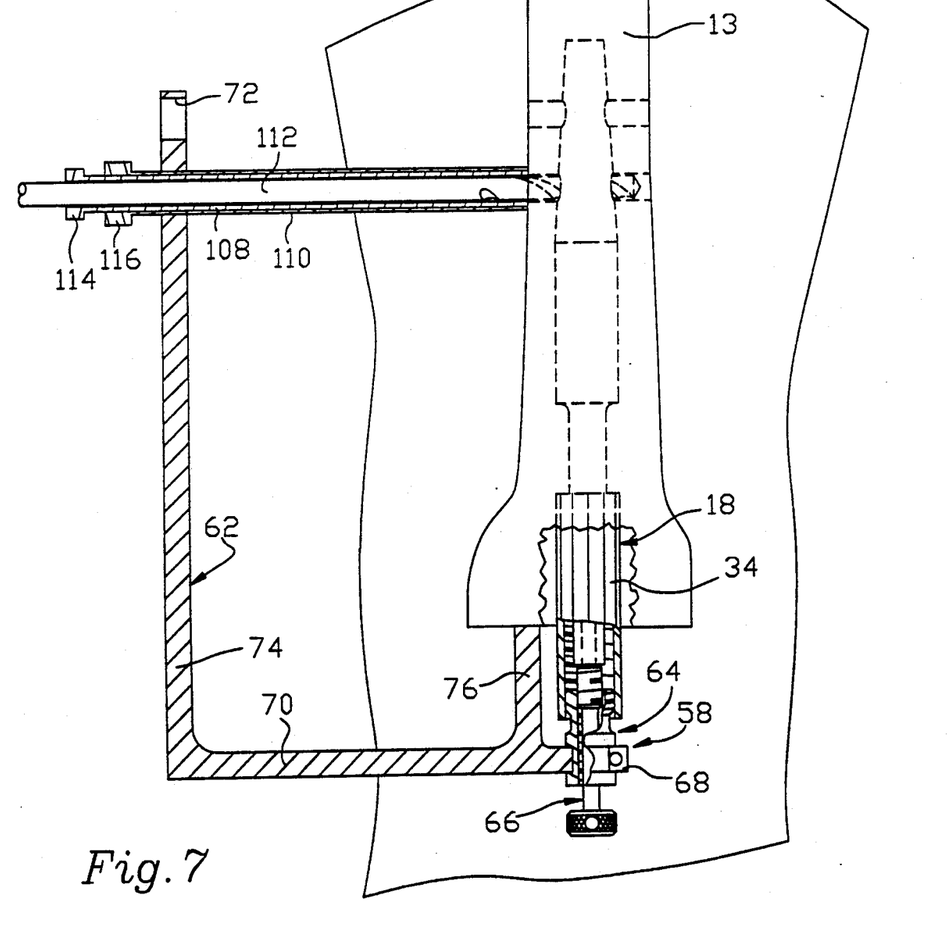
FIG. 7 is a front elevational view of a human femur illustrating the femoral base assembly, and a preferred femoral installation assembly used to implant the femoral base assembly.
Figure 8:
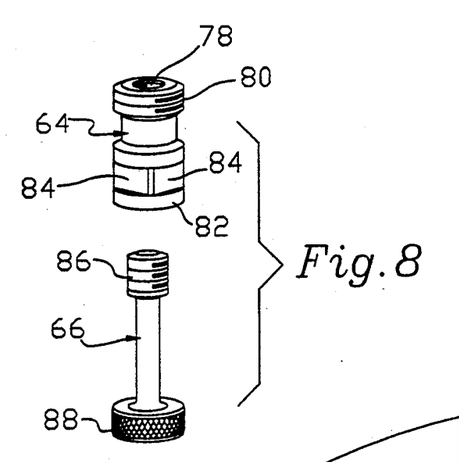
FIG. 8 is an exploded perspective view of an instrumentation plug and an adjustment bolt which form a part of the femoral installation assembly.
Figures 9, 10, 11:
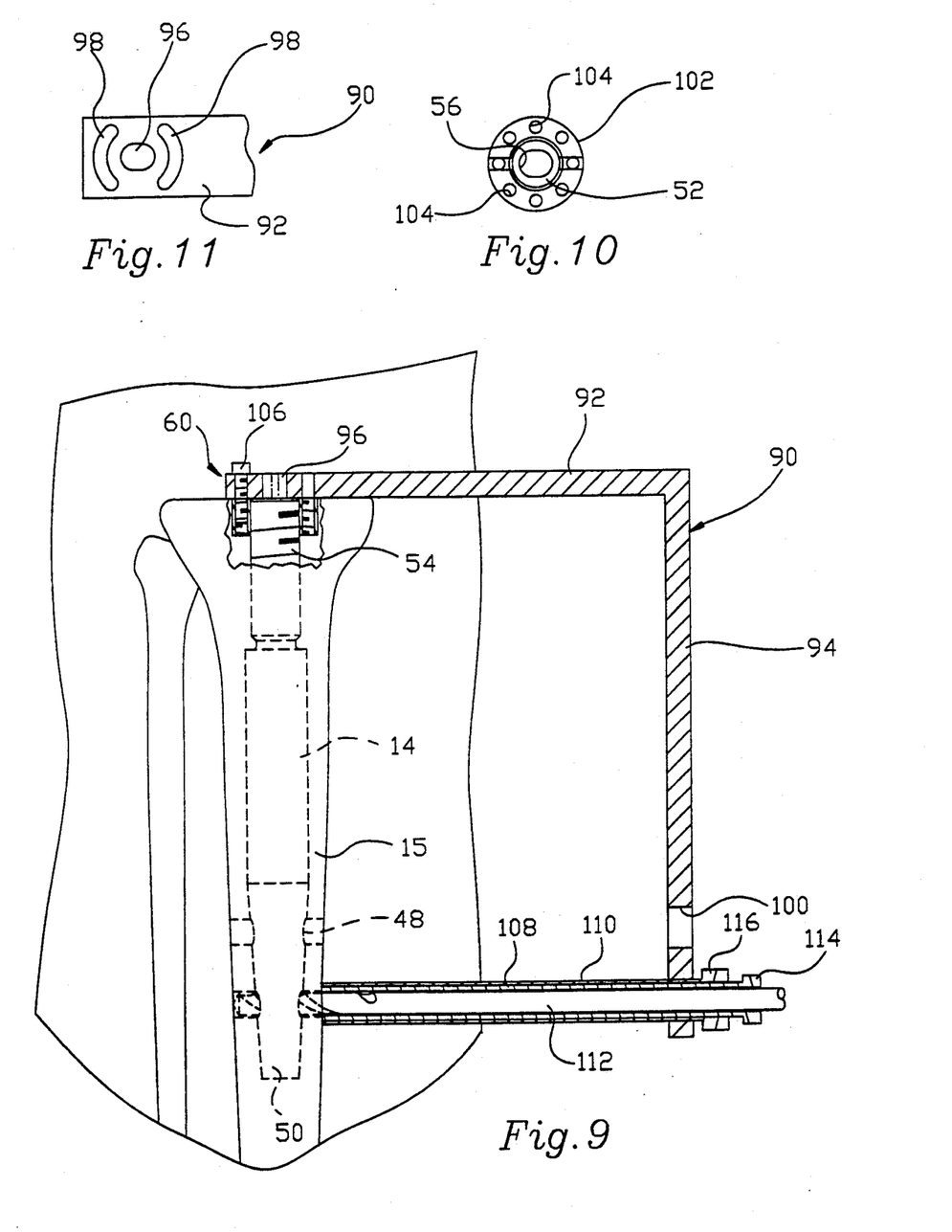
FIG. 9 is a front elevational view of a human tibia illustrating the tibial base, and a preferred tibial installation assembly; shown in section, used to implant the tibial base.
FIG. 10 is an end view of an instrumentation sleeve assembled on the tibial base.
FIG. 11 is a partial plan view of a tibial instrumentation bracket of the tibial installation assembly.

In order to assist the implantation of the intramedullary rod assembly, installation means are provided which include an installation assembly shown collectively in FIGS. 7-11. The installation assembly broadly includes a femoral base alignment assembly 58, as shown in FIGS. 7 and 8, and a tibial base alignment assembly 60 as illustrated in FIGS. 9-11.

As shown in FIG. 7, the femoral base alignment assembly 58 includes a femoral instrumentation bracket 62, an instrumentation plug 64 and an adjustment bolt 66. The bracket 62 is a generally L-shaped member having a notch 68 formed in the end of a first leg 70 thereof and a pair of transverse holes 72 extending through a second leg 74. A positioning flange 76 is formed in the first leg 70 adjacent the notch 68 and extends in a direction parallel with the second leg 74.

The instrumentation plug 64 is a hollow cylindrical member as shown in FIG. 8, and includes a threaded inner surface 78 and an outer surface which is provided with a threaded portion 80 adjacent a proximal end thereof. The plug 64 also includes a distal end portion 82 provided with a plurality of flat surfaces 84 extending therearound. The adjustment bolt 66 includes a threaded outer surface portion 86 adapted to mate with the threaded inner surface 78 of the plug 64, and is provided with a knurled gripping means 88 to facilitate handling thereof.

As shown in FIG. 9, the tibial base alignment assembly 60 includes a tibial instrumentation bracket 90 of generally L-shaped construction having first and second legs 92, 94. The free end of the first leg is shown in FIG. 11, and includes a pin 96 formed at least partially with an oval cross-sectional shape and adapted to be received in the bore 56 of the tibial base 14. An arcuate aperture 98 is located on each side of the oval aperture. Returning to FIG. 9, the second leg 94 of the instrumentation bracket 90 is formed with a pair of transverse holes 100 adjacent the free end thereof. As illustrated in FIG. 10, the tibial base alignment assembly 60 also includes an annular instrumentation sleeve 102 having a threaded central aperture adapted to mate with the threaded outer surface 54 of the tibial base 14, and a plurality of circumferential apertures 104 extending in a direction generally parallel with the central aperture thereof. Each of the circumferential apertures are threaded for receipt of a retaining bolt 106, as shown in FIG. 9.

The installation assembly also includes inner and outer sleeve 108, 110 members as shown in FIG. 7. The outer sleeve member 110 is hollow and includes an outer diameter adapted to be slidingly received within the transverse holes 72, 100 of the femoral and tibial instrumentation brackets 62, 90. The inner diameter of the outer sleeve 110 is adapted to receive the inner sleeve 108 when both sleeves are received within one of the transverse holes 72, 100. The inner sleeve 108 is also hollow and includes an inner diameter adapted to guide a drill bit 112 during implantation of the apparatus in a manner described more fully below. Each of the sleeves 108, 110 include knurled gripping means 114, 116 adjacent one end thereof for facilitating handling of the sleeves during surgery.

As shown in FIG. 2, the intramedullary rod assembly 10 is constructed by first positioning the slider 18 on the distal end 30 of the femoral base 12 and, thereafter, fitting the femoral plug 20 on the femoral base such that a friction fit is formed between the base and the plug. Once the femoral base assembly 12 is put together in this manner, the slider 18 is permitted to move axially relative to the femoral base 16 along the distal end thereof by a distance limited by engagement of the slider with the annular shelf 44 of the femoral plug 20, and the slider is freely rotatable relative to the femoral base.

After the slider 18 and plug 20 have been assembled on the femoral base 16, the intramedullary rod assembly 10 is ready for implantation. However, prior to installing the assembly, the femoral and tibial alignment assemblies 58, 60 are arranged on the femoral base assembly 12 and the tibial base 14 in a manner as shown in FIGS. 7 and 9.

Turning first to FIG. 7, the femoral instrumentation bracket 58 is arranged on the femoral base 16 by first threading the adjustment bolt 66 partially through the instrumentation plug 64 and threading the instrumentation plug partially into the distal end of the slider 18. Thereafter, the femoral instrumentation bracket 62 is fitted on the instrumentation plug 64 through receipt of opposed flat surfaces 84 of the plug in the notch 68 of the bracket, and the transverse holes 72 in the bracket are aligned with the transverse holes in the femoral base by inserting the inner and outer sleeves 108, 110 into one of the holes 72 and adjusting the axial and rotative position of the bracket relative to the base until the inner sleeve aligns with one of the transverse holes 26 in the base 16. Once the holes 72 of the bracket 62 are aligned collinear with the holes 26 in the femoral base 16, the adjustment bolt 66 is threaded into the instrumentation plug 64 until the bolt engages the distal end of the femoral plug 20. When the adjustment bolt is tightened against the femoral base 16, the slider 18, instrumentation plug 64 and instrumentation bracket 62 are retained against further axial or rotative movement relative to the femoral base, and the assembled combination of elements may be handled either as a unitary assembly or the bracket may be removed and replaced as desired.

Turning to FIG. 9, the tibial instrumentation bracket 9 is attached to the tibial base 14 by first threading the instrumentation sleeve 102 onto the proximal end of the tibial base 14 by a distance sufficient to expose the proximal end of the base. Thereafter, the bracket 90 is positioned on the tibial base 14 with the oval pin 96 of the instrumentation bracket received in the oval bore 56 of the tibial base. The retaining bolt 106 is then inserted through one of the arcuate apertures 98 of the bracket 90 and into one of the threaded circumferential apertures 104 of the instrumentation sleeve 102, and is tightened so that the bracket is held in position on the tibial base. The oval pin 96 is formed in the tibial instrumentation bracket 90 with the largest diameter of the oval cross-sectional shape of the pin 96 arranged in alignment with the longitudinal axis of the first leg 92 of the bracket and parallel with the transverse holes 100 so that when the bracket is fitted on the tibial base 14 in the manner described, the holes 100 in the bracket are aligned collinear with the transverse holes 48 of the tibial base. Once assembled, the tibial base 14 and the tibial base alignment assembly 60 may be handled together as a unitary assembly.

Implantation of the preferred construction of the intramedullary rod assembly is discussed with reference to an arthrodesis or knee fusion operation as shown in FIGS. 1 and 6. Turning first to FIG. 1, normal surgical approach is made to the knee joint. If additional bone removal is required before the bone fusion, it is accomplished prior to implantation of the rod assembly 10. The medullary channels of the femur and tibia are reamed with a series of reamers to a desired diameter adapted to permit receipt of the assembly 10. Bone blocks are removed from the anterior distal end of the femur and anterior proximal end of the tibia to provide access to the apparatus during implantation.

Installation of the tibial base 14 is carried out first. The tibial base 14 is inserted into the medullary cavity of the tibia 15 with the instrumentation bracket 90 extending toward the medial or laterally inward side of the knee joint. The tibial base 14 is pushed axially into the medullary cavity until the first leg 92 of the instrumentation bracket 90 contacts the tibia 15.

The transverse holes of the instrumentation bracket 90 are used by the surgeon in determining the proper location in which to make an incision and drill holes through the tibia 15 so that screws 28 may be driven into the tibia through the transverse holes 48 of the tibial base 14. By inserting the outer and inner sleeves 110, 108 into each of the transverse holes 100 and pushing the sleeves into contact with the tibia after an incision has been made and the tissue surrounding the tibia moved, a tap drill 112 is guided through the inner sleeve 108 into contact with the tibia to carry out a drilling operation as shown in FIG. 7. This operation is carried out with respect to each of the two transverse holes 48 of the tibial base 14.

After the holes have been formed in the tibia 15, the inner sleeve 108 is removed and a bone screw 28 is passed through the outer sleeve 110 into each of the holes 48 and is secured to the tibia as shown in FIG. 1. Once attachment of the tibial base 14 to the tibia is accomplished, the instrumentation bracket 90 and instrumentation sleeve 102 are removed from the tibial base 14.

The femoral base assembly 12, with the alignment assembly 58 attached thereto, is pushed into the medullary cavity of the femur 13 until the positioning flange 76 of the instrumentation bracket 62 contacts the femur. The instrumentation bracket 62 is used to assist the installation of the femoral base assembly 12 and is oriented during installation such that the second leg 74 of the bracket 62 is disposed laterally outward of the knee joint when the base assembly 12 is implanted.

The transverse holes 72 of the instrumentation bracket 62 are used in determining the proper location in which to make an incision and drill holes through the femur so that screws may be driven into the femur and through the transverse holes 26 of the femoral base 16. This operation is carried out with respect to each of the two transverse holes 26.

After holes have been formed in the femur, the inner sleeve 108 is removed and a bone screw 28 is passed through the outer sleeve 110 into each of the holes and is secured to the femur 13 as shown in FIG. 1. Once attachment of the femoral base assembly 12 is accomplished, the instrumentation bracket 62, instrumentation plug 64 and adjustment bolt 66 may be removed from the femoral base assembly and the slider 18 may be moved toward the proximal end of the femur.

Once the femoral base assembly 12 and the tibial base 14 have been attached to the femur 13 and tibia 15, the leg of the patient is lifted so that the tibia is aligned with the femur. As shown in FIG. 6, once this alignment is achieved, the circular-shaped distal end portion 46 of the femoral plug 20 is inserted into the oval bore 56 of the tibial base 14 and the rotational orientation of the tibial base is adjusted, if necessary, in order to align the oval-shaped portion of the femoral plug with the bore 56. Thereafter the slider 18 is attached to the tibial base via the threaded connection between the proximal end 52 of the tibial base 14 and the threaded inner surface 40 of the slider 18. Continued threading of the slider 18 onto the tibial base 14, as carried out by a wrench of conventional construction, moves the slider up against the annular shelf 44 of the femoral plug 20 and pulls the tibial base 14 axially toward the femoral base 16 such that the distance between the transverse holes 26 of the femoral base and the transverse holes 48 of the tibial base 14 is shortened. In this manner, the femur 13 and tibia 15 are pulled together in a direction along the longitudinal axes of the femoral and tibial bases 16, 14 until the femur and tibia come into contact and press against one another. The amount of compression exerted by the bones on one another is controlled by adjusting the relative position of the slider 18 on the tibial base 14.

After the intramedullary rod assembly 10 has been implanted in the manner described, bone fragments captured during formation of the windows are replaced and the knee is closed in a conventional manner.

If it becomes necessary at a later date to remove the intramedullary rod assembly 10, it is only necessary to perform the installation steps in inverse order such that the femoral and tibial bases 16, 14 may be separated from one another and independently removed from the femur and tibia respectively.

Although the invention has been described with reference to the illustrated preferred embodiment, it is noted that substitutions may be made and equivalents employed herein without departing from the scope of the invention as recited in the claims. For example, the tibial base may be produced in an assortment of sizes varying in outside diameter in order to accommodate patients having various tibia sizes, and the femoral base could be formed of multiple sizes as well.

Further, the basic geometry of the components could be changed without creating a detrimental effect upon the operation of the inventive apparatus. For example, the femoral base assembly and tibial base could be reversed such that the femoral base assembly is implanted in the tibia while the tibial base is implanted in the femur. Also, the proximal end of the tibial base could be provided with an internally threaded surface adapted to receive an outer threaded surface provided on the slider. This reversal of the threaded connection between the slider and tibial base would not necessarily effect the operation of the apparatus. It would also be possible to completely replace the threaded connection between the femoral and tibial bases by employing a ratchet mechanism or the like therebetween which would permit the assembly to operate in a manner similar to that described above.

What is claimed is:

1. An orthopaedic surgical implant apparatus for use in uniting a pair of bone segments wherein each of the bone segments includes a medullary cavity, the apparatus comprising:

an elongated intramedullary rod assembly defining a central longitudinal axis when assembled and including first and second points of attachment, the rod assembly being adapted to be positioned within the medullary cavities of the bone segments and secured to the first bone segment at the first point of attachment and to the second bone segment at the second point of attachment, the first and second points of attachment being separated in the direction of the longitudinal axis of the rod assembly by a predetermined distance the intramedulary rod assembly including a first base assembly on which the first point of attachment is provided, and a second base on which the second point of attachment is provided, the first base assembly and the second base being separable from one another and including means for preventing relative rotational movement therebetween when assembled;

tension means for shortening the predetermined distance between the first and second points of attachment of the rod assembly in the direction of the longitudinal axis after the rod assembly has been connected to the first and second bone segments so that the first and second bond segments are brought into contact with and press against one another; and extension limiting means for preventing the first and second points of attachment from being separated in the direction of the longitudinal axis by a distance greater than the shortened distance so as to prevent axial extension of the bone segments.

2. The implant apparatus as recited in claim 1, wherein the tension means permits additional reduction of the predetermined distance between the first and second points of attachment when an axial compressive load is applied on the rod assembly through the first and second points of attachment.

3. The implant apparatus as recited in claim 1, wherein the first base assembly and second base are formed of a material selected from the group consisting of cobalt-chromium, stainless steel, titanium alloys, and elemental titanium.

4. The implant apparatus as recited in claim 1, wherein the first base assembly and second base are formed of a material selected from the group consisting of a polymer and fiber composite.

5. The implant apparatus as recited in claim 1, wherein the tension means is adjustable to permit an infinite variation in the amount of shortening in the predetermined distance between the first and second points of attachment of the rod assembly.

6. The implant apparatus as recited in claim 1, further comprising installation means for positioning the first base assembly and the second base relative to the first and second bone segments during implantation of the apparatus, the installation means including locating means for indicating the location of the first and second points of attachment of the rod assembly to assist connection of the rod assembly to the pair of bone segments.

7. An orthopaedic surgical implant apparatus for use in uniting a pair of bone segments wherein each of the bone segments includes a medullary cavity, the apparatus comprising:

an elongated intramedullary rod assembly defining a central longitudinal axis when assembled and including first and second points of attachment, the rod assembly being adapted to be positioned within the medullary cavities of the bone segments and secured to the first bone segment at the first point of attachment and to the second bone segment at the second point of attachment, the first and second points of attachment being separated in the direction of the longitudinal axis of the rod assembly by a predetermined distance; and tension means for shortening the predetermined distance between the first and second points of attachment of the rod assembly in the direction of the longitudinal axis after the rod assembly has been connected to the first and second bone segments so that the first and second bone segments are brought into contact with and press against one another wherein the intramedullary rod assembly includes a first base assembly including the first point of attachment, a first base, a slider retained on the first base, and retaining means for retaining the slider on the first base while permitting movement of the slider within a predetermined range of movement in the direction of the longitudinal axis, and a second base including the second point of attachment, the first base assembly and the second base being separable from one another and including means for preventing relative rotational movement therebetween when assembled, the slider and the second base being provided with fastening means for securing the second base to the slider.

8. The implant apparatus as recited in claim 7, wherein the slider is rotatable relative to the first base and the fastening means includes a threaded connection between the slider and the second base.

9. An orthopaedic surgical implant apparatus for use in uniting a pair of bone segments wherein each of the bone segments includes a medullary cavity, the apparatus comprising:

an elongated intramedullary rod assembly defining a central longitudinal axis when assembled and including first and second points of attachment, the rod assembly being adapted to be positioned within the medullary cavities of the bone segments and secured to the first bone segment at the first point of attachment and to the second bone segment at the second point of attachment, the first and second points of attachment being separated in the direction of the longitudinal axis of the rod assembly by a predetermined distance and including;

holes passing through the first and second bases in a direction transverse the longitudinal axis; and tension means for shortening the predetermined distance between the first and second points of attachment of the rod assembly in the direction of the longitudinal axis after the rod assembly has been connected to the first and second bone segments so that the first and second bone segments are brought into contact with and press against one another.

10. An orthopaedic surgical implant apparatus for use in uniting a pair of bone segments wherein each of the bone segments includes a medullary cavity, the apparatus comprising:

an elongated intramedullary rod assembly defining a central longitudinal axis when assembled and including first and second points of attachment, the rod assembly being adapted to be positioned within the medullary cavities of the bone segments and secured to the first bone segment at the first point of attachment and to the second bone segment at the second point of attachment, the first and second points of attachment being separated in the direction of the longitudinal axis of the rod assembly by a predetermined distance, the intramedullary rod assembly including a first base assembly including the first point of attachment, and a second base including the second point of attachment, the first base assembly and the second base being separable from one another and including means for preventing relative rotational movement therebetween when assembled;

tension means for shortening the predetermined distance between the first and second points of attachment of the rod assembly in the direction of the longitudinal axis after the rod assembly has been connected to the first and second bone segments so that the first and second bone segments are brought into contact with and press against one another; and installation means for positioning the first base assembly and the second base relative to the first and second bone segments during implantation of the apparatus, the installation means including a first installation assembly provided with a first bracket and first bracket attachment means for securing the first bracket to the first base assembly in a predetermined orientation in which the locating means indicates the position of the first point of attachment, and a second installation assembly provided with a second bracket and a second bracket attachment means for securing the second bracket to the second base in a predetermined orientation in which the locating means indicates the position of the second point of attachment.

11. An orthopaedic surgical method of uniting a pair of bone segments wherein each of the bone segments includes a medullary cavity, the method comprising the steps of:

positioning a first base assembly of an intramedullary rod assembly within the medullary cavity of one of the bone segments and a second base of the intramedullary rod assembly within the medullary cavity of the other bone segment, the rod assembly defining a central longitudinal axis when assembled;

securing the first base assembly against axial and rotational movement relative to the one bone segment at a first point of attachment of the first base assembly and securing the second base against axial and rotational movement relative to the other bone segment at a second point of attachment of the second base, connecting the first base assembly with the second base to position the second point of attachment a predetermined distance from the first point of attachment in the direction of the longitudinal axis;

shortening the predetermined distance between the first and second points of attachment in the direction of the longitudinal axis after the rod assembly has been connected to the first and second bone segments so that the first and second bone segments are brought into contact with and press against one another; and preventing the first and second points of attachment from being separated in the direction of the longitudinal axis by a distance greater than the shortened distance so that axial extension of the bone segments is precluded.

* * * * *